United States Patent [19]

Khuddus et al.

[11] Patent Number: 5,136,047

[45] Date of Patent: * Aug. 4, 1992

[54] PROCESS FOR PREPARING FLAME RETARDANT BISIMIDE PRODUCT

[75] Inventors: Mo A. Khuddus; David R. Brackenridge, both of Baton Rouge, La.

[73] Assignee: Ethyl Corporation, Richmond, Va.

[*] Notice: The portion of the term of this patent subsequent to Apr. 3, 2007 has been disclaimed.

[21] Appl. No.: 657,514

[22] Filed: Feb. 19, 1991

Related U.S. Application Data

[63] Continuation of Ser. No. 442,780, Nov. 28, 1989, abandoned, which is a continuation of Ser. No. 210,328, Jun. 23, 1988, Pat. No. 4,914,212.

[51] Int. Cl.$^5$ .................. C07D 405/04; C07D 405/06
[52] U.S. Cl. ..................... 548/462; 548/461
[58] Field of Search ..................... 548/462, 461

[56] References Cited

U.S. PATENT DOCUMENTS

| | | | |
|---|---|---|---|
| 3,868,388 | 2/1975 | Dotson et al. | 548/462 |
| 3,966,726 | 6/1976 | Toth et al. | 544/204 |
| 4,092,345 | 5/1978 | Wolford et al. | 562/480 |
| 4,125,535 | 11/1978 | Wolford | 548/462 |
| 4,374,220 | 2/1983 | Sonnenberg | 524/94 |
| 4,535,170 | 8/1985 | Sonnenberg | 548/462 |
| 4,581,396 | 4/1986 | Sonnenberg | 524/87 |
| 4,914,212 | 3/1990 | Khuddus | 548/461 |
| 4,990,626 | 2/1991 | Hutchinson et al. | 548/462 |
| 4,997,953 | 3/1991 | McKenna | 548/461 |

FOREIGN PATENT DOCUMENTS

| | | |
|---|---|---|
| 0023420 | 2/1981 | European Pat. Off. |
| 2926638 | 1/1981 | Fed. Rep. of Germany |

Primary Examiner—Mary C. Lee
Assistant Examiner—Jacqueline Haley
Attorney, Agent, or Firm—Edgar E. Spielman, Jr.

[57] ABSTRACT

This invention relates to a process for preparing a white flame retardant product which principally contains a bisimide. The process comprises: providing an essentially water-free solution containing tetrabromophthalic anhydride and a solvent in a reaction vessel; forming a reaction mass by adding a diamine or a diamine salt to the solution at an addition rate such that, at the addition temperature, water formed during the addition is removed from the reaction mass substantially as it is formed; terminating the addition of the diamine when the molar ratio of the tetrabromophthalic anhydride initially present in the solution to the diamine or diamine salt added is at least about 2.00:1; maintaining the reaction mass at a temperature of at least 125° C. for at least 0.5 hr after the addition; and recover from the reaction mass the flame retardant product.

1 Claim, No Drawings

PROCESS FOR PREPARING FLAME RETARDANT BISIMIDE PRODUCT

This application is a continuation of application Ser. No. 442,780, filed Nov. 28, 1989, now abandoned, which in turn is a continuation of application Ser. No. 210,328, filed Jun. 23, 1988, now U.S. Pat. No. 4,914,212.

BACKGROUND OF THE INVENTION

This invention relates to improved halogenated bisimide flame retardant products, to their manufacture, and to compositions containing a flammable material and such flame retardant products.

As is taught in U.S. Pat. No. 4,374,220, there are a multitude of halogenated bisimides which are effective as flame retardants in formulation with macromolecular flammable materials, e.g. polymers. These formulations are useful in making articles such as wire insulation and electronic housings. Of the halogenated bisimides, the N,N'-alkylene-bis-(tetrabromophthalimide)s are especially commercially significant.

A presently used commercial route for producing a product which principally contains N,N'-alkylene-bis-(tetrabromophthalimide) comprises reacting tetrabromophthalic anhydride with a diaminoalkane in the presence of water and an alkanoic acid to yield a reaction mass containing the intermediate, N,N'-alkylene diammonium-bis-(tetrabromophthalate). The reaction mass is then heated to about 210° C. for a period of about 8 hours to convert the intermediate to N,N'-alkylene-bis-(tetrabromophthalimide) which is the principal constituent of the product recovered from the reaction mass. This product is particularly useful as it has good thermal stability and resistance to UV degradation. However, the product has a yellow color which argues against its presence in compositions used for forming white articles. Also, the intensity of the yellow color can vary between product batches, which color variance makes it difficult for the article manufacturer to maintain consistency in the color of the articles produced. The yellow color is believed to be due to impurities formed during the conversion of the N,N',-alkylene diammonium-bis-(tetrabromouphthalate intermediate to the corresponding bisimide product.

It is, therefore, an object of this invention to provide a process for producing a white flame retardant product which principally contains N,N'-alkylene-bis-(tetrabromophthalimide) or N,N'-bis-(tetrabromophthalimide), which product has high thermal stability and resistance to UV degradation.

It is also an object of this invention to provide a formulation which contains a macromolecular flammable constituent and the product of this invention wherein the color of articles formed from the formulation are not significantly affected by a yellow color contribution from the product during article formation

THE INVENTION

This invention relates to a process for preparing a flame retardant product which principally contains N,N'-alkylene-bis(tetrabromophthalimide) or N,N'-bis-(tetrabromophthalimide). The process features: providing, in a reaction vessel, an essentially water-free solution containing tetrabromophthalic anhydride and a solvent which contains at least about 15 wt % of a mono-, di- or tri- carboxylic acid having a dissociation constant not higher than $8.5 \times 10^{-5}$ at 25° C.; forming, at a temperature of at least 125° C., a reaction mass by adding to the solution a diamine or a diamine salt formed by the partial or total diamine neutralization of a mono-, di- or tri- carboxylic acid having a dissociation constant not higher than $8.5 \times 10^{-5}$ at 25° C.; removing water from the reaction mass substantially as the water is formed therein; terminating the addition of the diamine or diamine salt when the molar ratio of the tetrabromophthalic anhydride initially present in the solution to said diamine or diamine salt added is within the range of from about 2.00:1 to about 2.07:1; maintaining the reaction mass at a temperature of at least 125° C. for at least 0.5 hour after the addition of the diamine or diamine salt; and recovering from the reaction mass the flame retardant product.

It is theorized, but the process of this invention is not limited to such theory, that the following occurs during the process. The added diamine or diamine salt reacts quickly with the tetrabromophthalic anhydride to yield the intermediate, N,N'-(R)$_b$-bis-(tetrabromophthalamidic acid)—R and b are hereinafter defined. The intermediate then, more slowly, undergoes cyclization by losing water to form the desired N,N'-(R)$_b$-bis-tetrabromophthalimide. Based upon water recovery, it is observed that approximately 50% of the intermediate cyclization occurs during the above described addition of the diamine or diamine salt to the solution. The remaining cyclization occurs over a period of time, say from about, 0.5 to about 10.0 hours, during the post-addition temperature maintenance of the reaction mass. It is important to quickly remove the cyclization formed water during the diamine or diamine salt addition as the presence of such water during the addition results in the production of color causing impurities. After the diamine or diamine salt addition is at least substantially complete, quick water removal is not critical as the formation of such color causing bodies is less likely. Later in the description of the invention, further details concerning the formation of the color causing bodies will be presented.

For the purposes of this disclosure, the N,N'-(R)$_b$-bis-(tetrabromophthalamidic acid) intermediate will hereinafter be referred to as the intermediate and is represented by the formula,

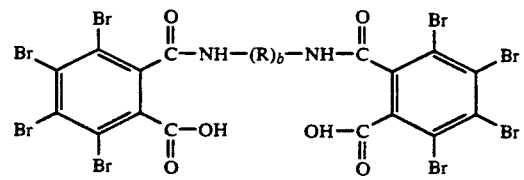

wherein R is an alkylene radical containing 1 to 6 carbon atoms and b is 1 or 0. R can be a branched or be a straight chain radical. R is preferably methylene, (—CH$_2$—), or ethylene, (—CH$_2$—CH$_2$—). When b is 0, the bonding between the two cyclic groups is via a N—N bond.

Also, for the purposes of this disclosure, the N,N'-alkylene-bis-(tetrabromophthalimide) and the N,N'-bis-(tetrabromophthalimide) will hereinafter be referred to collectively as bisimide and are represented by the formula,

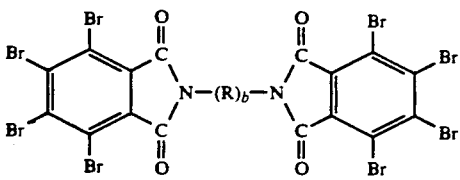

wherein R and b are as previously defined.

The diamine that is used in the process of this invention can be represented by the formula: $H_2N-(R)_b-NH_2$ wherein R and b are as previously defined. For example, the diamine can be 1,2-diaminoethane, 1,2-diaminopropane, 1,3-diaminopropane, 1,4-diaminobutane, 1,5-diaminopentane, 1,6-diaminohexane, hydrazine, etc. The diamine reactant can also be a mixture of diamines, however, the final product obtained will not be a single specie but rather will be a mixture of species as determined by the diamine mixture used. Preferred diamines are hydrazine and 1,2-diaminoethane as they yield particularly useful white flame retardant products. The diamine can be added neat or in solution with a solvent, e.g. o-, m-, p- xylene or a mixture thereof.

The partially or totally diamine neutralized mono-, di-or tri- carboxylic acid salts used in the practice of this invention will, hereinafter, simply be referred to as diamine salts. The carboxylic acid constituent of the diamine salt is derived from an acid having a dissociation constant not greater than about $8.5 \times 10^{-5}$ at 25° C. The preferred derivative acids are alkanoic and aralkanoic carboxylic acids containing 2 to 12 carbon atoms and mixtures thereof. Most preferred of these acids are those containing 2 to 6 carbon atoms. Exemplary of suitable derivative carboxylic acids are: acetic acid, propionic acid, isobutyric acid, valeric acid, hexanoic acid, phenylacetic acid, p-methylphenylacetic acid, alpha-phenylpropionic acid, succinic acid, glutaric acid, adipic acid, and mixtures thereof. Propionic acid is preferred. The cationic diamine constituent of the diamine salt can be derived from the $H_2N-(R)_b-NH_2$ diamines and the mixtures thereof which are discussed above. Preferred salts are the hydrazine and ethylene diamine salts. Especially preferred are the hydrazine and ethylene diamine salts of propionic acid.

The solvent used in the process of this invention is one in which the tetrabromophthalic anhydride is soluble and in which the intermediate and the bisimide product are substantially insoluble Further, the solvent should not adversely affect the yield, the color or the physical characteristics of the bisimide product. Since quick water removal during the diamine or diamine salt addition is an important feature of this invention, and since such removal is conveniently effected by boiling the water from the reaction mass, it is preferred that the solvent have a boiling point which is about 25° C. above the boiling point of water at the reaction pressure. Thus, if the reaction is run at atmospheric pressure then the solvent boiling point can be preferably within the range of from about 125° C. to about 170° C. The use of solvents having a boiling point, at atmospheric pressure, much in excess of 170° C., say 230° C., are not preferred as it is economically difficult to thermally remove them from the final bisimide product. If the quick removal of water from the reaction mass is achieved by chemical or mechanical means and not by boiling, then the solvent boiling point need not be 25° C. above that of water as discussed above. Rather, the solvent can have a boiling point as low as that which the reaction temperature and the reaction pressure will provide. Chemical removal can be effected by the use, in the reaction mass, of a dehydrating agent, e.g. propionic anhydride, acetic anhydride, phosphorus pentoxide, etc. The use of molecular sieves illustrates a means for mechanical water removal.

The solvent can be comprised of a single constituent or a plurality of constituents. A necessary constituent is a mono-, di- or tri- carboxylic acid having a dissociation constant not higher than $8.5 \times 10^{-5}$ at 25° C. Exemplary of suitable carboxylic acids are: acetic acid, propionic acid, isobutyric acid, valeric acid, hexanoic acid, phenylacetic acid, p-methylphenylacetic acid, alpha-phenylpropionic acid, succinic acid, glutaric acid, adipic acid, and mixtures thereof. Preferred carboxylic acids are the alkanoic and the aralkanoic carboxylic acids containing 2 to 12 carbon atoms, with those acids containing 2 to 6 carbon atoms being more preferred. A most preferred acid is propionic acid. Quantitatively, the mono-, di- or tri- carboxylic acid is present in the solvent in an amount in excess of about 15 wt %, based upon the total weight of the solvent. Preferred amounts are within the range of from about 25 wt % to about 100 wt %. Most preferred amounts are 30 wt % and 100 wt %.

A second useful constituent is an aromatic hydrocarbon or an aromatic halohydrocarbon which is liquid under reaction conditions. Preferred of these aromatics are those which have a boiling point above about 80° C. at atmospheric pressure. Examples of suitable aromatic compounds are: benzene; o-, m-, p- xylene, and mixtures of such xylenes; mesitylene; cumene; pseudocumene; o-, m-, p- diethylbenzene, and mixtures of such diethylbenzenes; ethylbenzene; o-, m-, p- dichlorobenzenes, and mixtures of such dichlorobenzenes; chlorobenzene; and mixtures of the foregoing. Preferred are o-, m-, p- xylene and mixtures thereof.

The solvent may contain other constituents which may or may not contribute to the solvent function provided that such constituents do not unduly interfere with the process or with the quality of the bisimide product.

One preferred solvent is comprised essentially of propionic acid, say about 99+ wt % propionic acid. Other preferred solvents are those which contain from about 85 wt % to about 70 wt % o-, m- or p- xylene or mixtures thereof, and from about 15 wt % to about 30 wt % propionic acid, all based upon the total weight of the solvent.

The tetrabromophthalic anhydride/solvent solution provided to the reaction vessel can be formed in the reaction vessel or can be formed exteriorly of the reaction vessel and then added thereto. Since the solution needs to be substantially water-free, it is good practice to treat the solution prior to its use in the process to remove any water present. Such water removal can easily be accomplished by refluxing the solution to evolve therefrom any water present.

The reaction between the tetrabromophthalic anhydride and the diamine or the diamine salt to produce the intermediate should occur at a temperature above about 125° C. Temperatures of about 115° C. or lower yield a bisimide product which is off color. A preferred reaction temperature is within the range of from about 130° C. to about 135° C. Since the minimum 125° C. reaction temperature is well above the boiling point of water at atmospheric pressure, the removal of the water from the reaction mass is conveniently effected thermally, i.e.

by boiling the water out of the reaction mass. However, if the removal of water is to be accomplished by chemical or mechanical means, it may be desirable to avoid boiling the water. This can be accomplished by operating the process under a superatmospheric pressure. Chemical or mechanical water removal does not, however, prohibit operation of the process at atmospheric pressure as removal of water by boiling and by chemical or mechanical means may be combined.

As before stated, the rate of addition of the diamine or diamine salt reactants to the solution needs to be such that the water formed during such addition is removed from the solution substantially as it is formed. Thus, the rate of addition is coupled to the rate of water removal, be it by boiling, chemical means or by mechanical means. (By removal it is meant that the water is physically removed from the reaction mass, chemically changed, or is rendered inactive by mechanical means or by chemical bonding.) If the water is not so removed, it is believed that it will react with the tetrabromophthalic anhydride to form tetrabromophthalic acid which can form a salt with the diamine or with the cation portion of the diamine salt. It has been found that when this tetrabromophthalic acid salt impurity is present in the final bisimide product, that articles made from formulations containing such product will take on a yellow color under normal article forming conditions. Determination of the proper addition rate is made empirically considering the reaction temperature, process pressure, and, in the case of water removal by boiling, by monitoring the evolution of the produced water from the reaction mass and comparing same against the theoretical amount of water which should be produced by the reaction at the addition rate used. The rates of water removal for the chemical and mechanical techniques are usually determined by trial and error. Also to be considered is the process scale and the configuration of the reaction vessel used. It is understood that the instantaneous removal of the water as it is produced is impractical. However, water removal should be as expeditiously accomplished as is possible without use of process conditions or removal techniques which would adversely affect the bisimide product or slow the addition rate so that the process becomes uneconomical.

The quantitative relationship between the tetrabromophthalic anhydride and the diamine or diamine salt used can be either substantially stoichiometric, i.e. a molar ratio of anhydride to diamine of about 2.00:1, or can be in excess of stoichiometric, i.e. a molar ratio of anhydride to diamine of at least 2.03:1, which is about a 1.5% molar excess.

When the relationship is nearly stoichiometric, the bisimide product particle size can be very fine and, thus, difficult to recover from the reaction mass in a short period of time. Also, if the near stoichiometric relationship is used, the tetrabromophthalic anhydride will usually have to be treated before being used in the process should it contain certain impurities. These impurities generally include $Br_2$, $H_2SO_4$, and tetrabromophthalic acid, and are usually found in commercially-available tetrabromophthalic anhydride. From a color and a quantitative standpoint, the $Br_2$ is most troublesome. From an acid number standpoint, for the final bisimide product, the acids are most troublesome. The amount of $Br_2$ can be reduced greatly, say from 100 ppm to 10 ppm, by washing the tetrabromophthalic anhydride with an aqueous reducing agent, such as aqueous sodium hydrosulfite. With this treatment, the acid number can also be reduced from about 1.8 to about 0.6 mg KOH/g of sample. It is also possible to reduce the impurity concentration by heating the tetrabromophthalic anhydride to a temperature of about 200° C. for an hour or more.

When a molar excess of tetrabromophthalic anhydride of at least about 1.5% is used, the bisimide product filters quicker than when a stoichiometric amount of tetrabromophthalic anhydride is used. Also with such a molar excess, the tetrabromophthalic anhydride does not need pre-treatment despite the presence of the usual quantities of the impurities discussed above. While the use of a molar excess is preferred for the process of this invention, it is to be understood that large excesses, i.e. above 5%, are not desirable as significant quantities of unreacted tetrabromophthalic anhydride will be found in the bisimide product. Thus, a preferred molar excess is within the range of from about 1.5% to about 3.5%. The 3.5% excess approximates a molar ratio of anhydride to salt of about 2.070:1. A most highly preferred molar excess is within the range of from about 2.2% (molar ratio 2.040:1) to about 2.4% (molar ratio 2.048:1). An especially suitable molar excess is 2.3% (molar ratio 2.046:1). percentages and molar ratios are not corrected to account for the normal amount of impurities found in commercially available tetrabromophthalic anhydride and diamine. The commercially available tetrabromophthalic anhydride used in running the process of this invention was from 99.5 wt % to 100 wt % pure. The diamine used was generally about 99 wt % pure.

To effect the remaining cyclization of the intermediate after the diamine or diamine salt addition, the reaction mass is maintained at a temperature above about 125° C. until cyclization is substantially complete. The temperature is preferably within the range of from about 130° C. to about 165° C. and most preferably within the range of from about 130° C. to about 135° C. Using a temperature of at least 125° C., cyclization should be complete within from about 0.5 to about 10.0 hours. Determination of the completion of cyclization is conveniently based upon the direct or indirect observation of the cessation of water production. The cyclization water produced during this period is removed from the reaction mass, however, its rate of removal is not critical. Expeditious removal, though, is advantageous as it leads to shorter process times. Water removal can be accomplished by the same techniques used in effecting water removal during the diamine or diamine salt addition. The preferred technique is by boiling the water from the reaction mass as this technique is easily achieved by using the 125° C. or above temperature and the desirable atmospheric process pressure. Also, with boiling, the water production can easily be determined by monitoring the vapors evolving from the reaction mass for the presence of water.

The temperature maintenance during both the diamine or diamine salt addition step and the cyclization of the remaining intermediate step can most conveniently be effected by running the process under reflux conditions. Non-reflux conditions can be used but temperature maintenance must be monitored to keep the process temperature desired. Under reflux conditions, the solvent chosen must be suitable for refluxing. From this standpoint, particularly useful solvents for use under atmospheric or near atmospheric conditions are those which have a boiling point within the preferred range for each of the above steps, i.e. a range of from about 130° C. and 135° C.

After cyclization, it is preferred that the reaction mass undergo a digestion step, which step has been found to produce a bisimide product which can be filtered more quickly due to its larger particle size. The digestion can occur at atmospheric pressure and at a temperature of at least 125° C., and more preferably at a temperature within the range of from about 130° C. to about 135° C. The digestion period, when the temperature is 130° C. to 135° C., will be within the range of from about 1 to about 24 hours. Shorter digestion times can be effected by using higher temperature, e.g. 160° C. to 175° C. However, since it is preferred to run the digestion under refluxing conditions for temperature control purposes, super atmospheric pressure may be needed at these elevated temperatures depending upon the solvent used.

The bisimide product formed is a white precipitate and can be recovered from the reaction mass by any conventional means, e.g. filtration, centrifugation, etc. Since the recovered bisimide product initially contains up to about 50 wt % solvent from the reaction mass, a most expeditious way of simultaneously recovering the bisimide product and reducing its solvent content is centrifugation. Centrifuging the bisimide product can reduce the solvent content to about 15 wt %. It has also been found that the recovery rate of the bisimide product may be increased in some cases by effecting the filtration, centrifuging, etc. at a reaction mass temperature of from about 65° C. to about 85° C.

After recovery, the bisimide product is preferably washed with any of the solvent constituents, e.g. xylene, propionic acid etc., and then with a polar, non-aqueous solvent such as alcohol. After this last wash, the bisimide product is dried at a temperature of from about 110° C. to about 125° C. for about 16 hours.

To further purify the flame retardant product, oven aging can be utilized. Generally, oven aging occurs over a period of from about 8 to about 16 hours and at a temperature of from about 180° C. to about 250° C. Oven aging reduces the amount of solvent and other volatile impurities present, thereby yielding a very pure bisimide product.

The bisimide product produced by the process of this invention not only has good thermal stability and resistance to UV degradation, but also has a low acid number, less than about 1, and a high bromine content, i.e. within the range of from about 66% to about 67%. Acid numbers within the range of from about 0.20 to about 0.95 are characteristic of the bisimide product. Hunter Colorometer values for the bisimide product are exemplified by L =82.18, a = −1.63, b =5.31, and a yellowness index (Y.I.) =10.42, with the product having a particle size distribution of 90% <2.66 microns, 50% <1.73 microns and 10% <1.07 microns.

The bisimide product of this invention may be used as a flame retardant in formulation with virtually any flammable material. The material may be macromolecular, for example, a cellulosic material or a polymer. Illustrative polymers are: olefin polymers, cross-linked, and otherwise, for example, homopolymers of ethylene, propylene, and butylene; copolymers of two or more of such alkylene monomers, and copolymers of one or more of such alkylene monomers, and any other co-polymerizable monomers, for example, ethylene/propylene copolymers, ethylene/ethyl acrylate copolymers, and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene, and styrene; natural rubber; butyl rubber; and polysiloxanes. The polymer may also be a blend of various polymers. Further, the polymer may be, where appropriate, crosslinked by chemical means or by irradiation.

The amount of bisimide product used in a formulation will be that quantity needed to obtain the flame retardancy sought. It will be apparent to those skilled in the art that for all cases no single precise value for the proportion of the bisimide product in the formulation can be given, since this proportion will vary with the particular flammable material, the presence of other additives, and the degree of flame retardancy sought for in any given application. Further, the proportion necessary to achieve a given flame retardancy in a particular formulation will depend upon the shape of the article into which the formulation is to be made, for example, electrical insulation, tubing, and film will each behave differently. In general, however, the formulation may contain from about 3 to about 40 wt %, preferably 10 to 30 wt %, of the bisimide product when it is the only flame retardant compound in the formulation. The wt % amounts are based upon the total weight of the formulation.

It is especially advantageous to use the bisimide product of this invention and an inorganic compound, especially the oxide, of a Group V element, for example, bismuth, arsenic, phosphorus, and especially antimony, in the formulation. Of these compounds, antimony oxide is especially preferred. If such a compound is present in the formulation, the quantity of bisimide product needed to achieve a given flame-retardancy is accordingly reduced.

Formulations containing a bisimide product/inorganic compound flame retardant system may contain up to about 40% by weight of the system, preferably between 10 and 30% by weight.

It is believed that the bisimide product and the inorganic compound will react under the conditions of combustion of a flammable material to form inorganic bromine compounds, e.g., hydrogen bromide and oxybromides, which assist in retarding combustion. The bromine-bearing bisimide product also acts as a flame retardant independently, and the proportions of the bisimide product and inorganic compound in a flame retardant system are a matter of choice, depending on the material in which the system is to be incorporated and commercial considerations. Generally, the bisimide product and the inorganic compound are in a weight ratio of from about 1:1 to about 7:1, and preferably of from about 2:1 to about 4:1.

The formulations containing the bisimide product of this invention may contain any of the additives usually present in such formulations, e.g. plasticizers, antioxidants, filler, pigment, UV stabilizers, etc.

The inventions disclosed herein are illustrated by the following Examples.

EXAMPLE I

A water-free solution which contained 450 g of xylene, 195 g of propionic acid, and 174.1 g (0.375 mol, 0.05% molar excess) of commercially obtained tetrabromophthalic anhydride was charged to a suitable reaction vessel. The solution was heated to 127° C., and had added thereto, over a period of 0.5 hr, a solution of 11.2 g of ethylene diamine (0.187 mol, purity of 99% EDA was not corrected) and 5 g of xylene. The water of reaction was removed. The resultant reaction mass was heated to reflux (130° C.-133° C.) for about 5 hr while removing the water of reaction. The reaction mixture was then cooled to 25° C. and filtered to separate therefrom the solid product. The filtration took 40 min. to yield a 1.75-in.-thick cake. The cake was washed with 400 g of xylene, followed by 400 g of methanol, and then dried at 125° C.. All portions of the process were run at atmospheric pressure. The process resulted in a 93% recovered yield of white N,N'-ethylene-bis-tetrabromophthalimide product having a melting point of 460° C.-463° C., a bromine content of 66.6%, and an acid number of 1.8. The white product turned yellow to light-brown upon oven aging at 210° C. for 16 hr.

This product was formulated with poly(butyleneterephthalate) (PBT) resin by Brabender mixing at about 220° C. The formulation was compression molded at 232° C. and 20,000 psi (137,900 kPa) and gave light-yellow-colored bars.

This example illustrates that, when using a molar excess of less than 1.5%, a color problem will be encountered if the tetrabromophthalic anhydride feed is not pretreated to reduce the impurities contained therein.

EXAMPLE II

Water (1L) and 200 g of commercially obtained tetrabromophthalic anhydride were fed to a suitable reaction vessel and stirred well to give a uniform slurry. To this slurry was added 20 g of sodium hydrosulfite ($Na_2S_2O_4$) powder. The resultant mix was stirred for 10 to 30 min at 25° C. The product was recovered by filtering and then washed twice with 200 mL of water. After washing, the product was dried at 125° C. for 15 hr. The effect of this treatment on the tetrabromophthalic anhydride $Br_2$ content is shown in Table I.

TABLE I

|  | Tetrabromophthalic Anhydride | |
| --- | --- | --- |
|  | Before Treatment | After Treatment |
| Color | Off-white | White |
| Elemental bromine | 87 ppm | 9 ppm |

EXAMPLE III

Example I is repeated except that the commercially obtained tetrabromophthalic anhydride was first treated with sodium hydrosulfite as in Example II. The process gave a 93% recovered yield of white N,N'-ethylene-bis-tetrabromophthalimide product having a melting point of 460° C.-464° C., a bromine content of 66.6%, and an acid number of 0.6. The white product remained white with slight discoloration upon oven aging at 210° C. for 16 hr. Filtration times to obtain a 1.75-in. cake of product were 40 and 30 min at the filtration temperatures of 25° C. and 80° C., respectively.

Incorporation of this product into PBT resin by Brabender mixing at 220° C. and compression molding at 232° C. and 20,000 psi (137,900 kPa) gave white bars.

This example illustrates the color benefits obtained when the tetrabromophthalic anhydride is treated to reduce the impurities contained therein and when using near stoichiometric quantities of the anhydride in the process.

EXAMPLE IV

To a reaction vessel were charged 900 g of xylene, 400 g of propionic acid, and 348.2 g (0.751 mol, 2.3% molar excess) of sodium hydrosulfite-treated tetrabromophthalic anhydride. The solution was brought to reflux (130° C.-133° C.) for about 0.5 hr while removing water present in the raw materials. Then a solution comprised of 22 g of ethylene diamine (0.367 mol, 99% purity of EDA was not corrected) and 30 g of xylene was added to the reaction vessel over a period of 65 min. The produced water of reaction was contemporaneously removed at 130° C. The resultant reaction mass was heated to reflux (130° C.-133° C.) for an additional 6 hr to remove the remaining water of reaction. The reaction mass was then cooled to 80° C. and filtered to separate the solid product (1.75-in.-thick cake was obtained in 12 min). The product was washed twice with 800 g of xylene and dried at 125° C. for 16 hr. All process steps were run at atmospheric pressure. The process resulted in a 92% recovered yield of white N,N'-ethylene-bis-tetrabromophthalimide product having a melting point of 456° C.-458° C., a bromine content of 66.5%, and an acid number of 0.23. The white product remained white after oven aging at 210° C. for 16 hr.

This product was formulated with PBT resin by extrusion in a twin screw extruder at 250° C.-260° C.. Injection molding of the formulation at 250° C.-260° C. gave white bars.

EXAMPLE V

Example IV was repeated except that the ethylene diamine and xylene solution was added at 115° C.. The process resulted in a 92% recovered yield of a white product that turned yellow after oven aging at 210° C. for 16 hr.

This example illustrates the deleterious effect of not removing the cyclization-produced water from the reaction mass expeditiously. The low temperature, 115° C., was too low in view of the addition rate to achieve rapid water removal.

EXAMPLE VI

Example IV was repeated except that the sodium hydrosulfite-treated tetrabromophthalic anhydride was replaced with untreated commercially obtained tetrabromophthalic anhydride. The process resulted in a 91% recovered yield of white product having a melting point of 458° C.-460° C., a bromine content of 66.4%, and an acid value of 0.95. The white product remained white upon oven aging at 210° C. for 16 hr.

A formulation of this product with both PBT and high impact polystyrene (HIPS) resins was formed by extrusion in a twin screw extruder at 250° C.-260° C. The resultant formulation was injection molded (250° C.-260° C.) to yield white bars.

EXAMPLE VII

Example IV was repeated except that a 1:1 salt of ethylene diamine:propionic acid was used instead of the ethylene diamine and xylene solution. The process resulted in a 91% recovered yield of white product having a melting point of 454° C.–456° C., a bromine content of 66.5%, and an acid value of 0.28. The white product remained white upon oven aging at 210° C. for 16 hr.

A solution of 650 g of propionic acid and 174.1 g (0.375 mol, about a 0.05% molar excess) of untreated commercially obtained tetrabromophthalic anhydride was charged to a suitable reaction vessel. The solution was heated to 141° C. for 0.5 hr to remove water present in the raw materials. After the removal of water was accomplished, the solution was cooled to 137° C. and 11 g of neat ethylene diamine (0.183 mol, 99% purity of ethylene diamine was not corrected) was then added over a period of 10 min while the water of reaction was removed. After this addition, the reaction mass was heated for an additional 6 hr at 137° C.–143° C. while removing the water of reaction therefrom. The reaction mass was cooled to 80° C. and filtered to separate the solid product therefrom. The solid product was washed twice with 400 g of propionic acid, and dried at 125° C for 16 hr. The process resulted in a 90% recovered yield of N,N'-ethylene-bis-(tetrabromonaphthalimide) product having a melting point of 457° C.–458° C. and an acid value of 1.25. The white product remained white upon oven aging at 210° C. for 16 hr.

EXAMPLE IX

A glass-filled (30 wt %) PBT-based formulation containing 5 wt % antimony trioxide and 11 wt % of a bisimide product of this invention was blended and prepared by extrusion with a twin screw extruder at 250° C.–260° C. The formulation was then injection molded (250° C.–260° C.) to form test bars which were subjected to U.V. stability tests. For comparison purposes, test bars were produced in the same manner and with the same formulation except that Ethyl Corporation's Saytex ® BT-93 flame retardant was used instead of the bisimide product of this invention. The results were as follows:

| Test Bar | $\Delta E_{300}$ Xenon-Arc (ASTM D 4459) | $\Delta E$ HPUV (ASTM D 4674) |
|---|---|---|
| A[1] | 3.24 | 2.82 |
| B[2] | 1.71 | 0.57 |

[1] bar made from a formulation containing Saytex ® BT-93 flame retardant, which flame retardant is predominant in N,N'-ethylene-bis-(tetra-bromophthalimide).
[2] bar made from a formulation containing the bisimide product of this invention.

The foregoing results show that PBT formulations containing the bisimide product of this invention have good U.V. stability.

What is claimed:

1. In a process for increasing the particle size of a product predominant in N,N'-alkylene-bis(tetrabromophthalimide) or N,N'-bis(tetrabromophthalimide), said product being produced of the reaction of tetrabromophthalic anhydride and a diamine of the formula $H_2N—(R)_b—NH_2$ where R is methylene or ethylene and b =0 or 1, said reaction occuring in the presence of a solvent which contains at least about 15 weight percent of a mono-, di- or tri-carboxylic acid having a dissociation constant not higher than $8.5 \times 10^{-5}$ at 25° C., the improvement which comprises digesting said product at a temperature of at least 125° C. for a period of time within the range of from about 1 hour to about 24 hours to effect said increase in particle size.

* * * * *